(12) United States Patent
Mattoussi et al.

(10) Patent No.: US 9,446,153 B2
(45) Date of Patent: Sep. 20, 2016

(54) POLYETHYLENE GLYCOL BASED OLIGOMERS FOR COATING NANOPARTICLES, NANOPARTICLES COATED THEREWITH, AND RELATED METHODS

(71) Applicant: The Florida State University Research Foundation, Inc., Tallahassee, FL (US)

(72) Inventors: Hedi Mattoussi, Tallahassee, FL (US); Goutam Palui, Tallahassee, FL (US); Hyon Bin Na, Seoul (KR)

(73) Assignee: The Florida State University Research Foundation, Inc., Tallahassee, FL (US)

(*) Notice: Subject to any disclaimer, the term of this patent is extended or adjusted under 35 U.S.C. 154(b) by 0 days.

(21) Appl. No.: 14/838,611

(22) Filed: Aug. 28, 2015

(65) Prior Publication Data

US 2016/0055946 A1 Feb. 25, 2016

Related U.S. Application Data

(60) Division of application No. 13/772,632, filed on Feb. 21, 2013, now Pat. No. 9,309,432, which is a continuation-in-part of application No. 13/608,119, filed on Sep. 10, 2012, now abandoned.

(60) Provisional application No. 61/532,756, filed on Sep. 9, 2011.

(51) Int. Cl.
| | |
|---|---|
| *A61K 49/00* | (2006.01) |
| *H01F 1/00* | (2006.01) |
| *C08F 8/32* | (2006.01) |
| *C08F 20/06* | (2006.01) |
| *C08F 22/00* | (2006.01) |

(Continued)

(52) U.S. Cl.
CPC ............ *A61K 49/0067* (2013.01); *C08F 8/32* (2013.01); *C08F 20/06* (2013.01); *C08F 22/00* (2013.01); *C08K 5/00* (2013.01); *C08K 5/13* (2013.01); *C08L 33/00* (2013.01); *C08L 71/08* (2013.01); *C09D 133/14* (2013.01); *H01F 1/0054* (2013.01); *C08F 220/26* (2013.01)

(58) Field of Classification Search
CPC ... A61K 49/0067; H01F 1/0054; C08F 8/32; C08F 20/06; C08F 22/00; C08F 220/26; C08K 5/00; C08K 5/13; C08L 33/00; C08L 71/08; C09D 133/14
USPC ........... 524/431, 24, 45, 214, 226, 315, 502, 524/503, 535; 526/317.1, 318, 318.43, 320; 525/183, 182, 185
See application file for complete search history.

(56) References Cited

PUBLICATIONS

M. Stewart et al. "Multidentate Poly(ethylene glycol) Ligands Provide Colloidal Stability to Semiconductor and Metallic Nanocrystals in Extreme Conditions", J. Am. Chem. Soc., 2010, 132 (28), pp. 9804-9813.*

(Continued)

*Primary Examiner* — Michael M Bernshteyn
(74) *Attorney, Agent, or Firm* — Armstrong Teasdale LLP (57) ABSTRACT

In a composition aspect of the invention, a nanoparticle coating comprises repeating polyacrylic acid monomers covalently bound together in an aliphatic chain having a plurality of carboxylic acid functional groups and modified carboxylic acid functional groups extending therefrom. A first portion of the modified carboxylic acid functional groups are modified by a PEG oligomer having a terminal methoxy functional group and a second portion of the modified carboxylic acid functional groups are modified by a PEG oligomer having at least one terminal catechol group.

4 Claims, 5 Drawing Sheets

(51) Int. Cl.

| | |
|---|---|
| C08F 220/26 | (2006.01) |
| C08K 5/00 | (2006.01) |
| C08K 5/13 | (2006.01) |
| C08L 33/00 | (2006.01) |
| C08L 71/08 | (2006.01) |
| C09D 133/14 | (2006.01) |

(56) References Cited

PUBLICATIONS

W. Liu et al. "Compact Biocompatible Quantum Dots via RAFT-Mediated Synthesis of Imidazole-Based Random Copolymer Ligand", J. Am. Chem. Soc., 2010, 132, pp. 472-483.*

Alivisatos, A.P., Semiconductor Clusters, Nanocrystals, and Quantum Dots, Science; Feb. 16, 1996, vol. 271, No. 5251; ProQuest; pp. 933-937.

Murray, C. B., et al., Synthesis and Characterization of Monodisperse Nanocrystals and Close-Packed Nanocrystal Assemblies, Annu. Rev. Mater. Sci, 2000, vol. 30 pp. 545-610.

Klimov, V.I. et al., Optical Gain and Stimulated Emission in Nanocrystal Quantum Dots, Science, Oct. 13, 2000, vol. 290, No. 5490; ProQuest, pp. 314-317.

Malko, A.V. et al., From amplified spontaneous emission to microring lasing using nanocrystal quantum dots solids, Applied Physcis Letters, Aug. 12, 2002, vol. 81, No. 7, pp. 1303-1305.

Nozik, A. J. et al., Semiconductor Quantum Dots and Quantum Dot Arrays and Applications of Multiple Exciton Generation to Third-Generation Photovoltaic Solar Cells, Chem. Rev., 2010, vol. 110, pp. 6873-6890.

Li Ling et al., Highly Efficient CdS Quantum Dot-Sensitized Solar Cells Based on a Modified Polysulfide Electrolyte, Journal of the American Chemical Society, 2011, vol. 133, pp. 8458-8460.

Raymo, Francisco M., et al., Luminescent chemosensors based on semiconductor quantum dots, Physical Chemistry Chemical Physics, Feb. 1, 2007, vol. 9, pp. 2036-2043.

Medintz, Igor L., et al., Quantum dot bioconjugates for imaging labelling and sensing, Nature Materials, Jun. 2005, vol. 4, pp. 435-446.

Michalet, X. et al., Quantum Dots for Live Cells, in Vivo Imaging, and Diagnostics, Science, Jan. 28, 2005, vol. 307, pp. 538-544.

Biju, Vasudevanpillai et al., Delivering quantum dots to cells: bioconjugated quantum dots for targeted and nonspecific extracellular and intracellular imaging, Chemical Society Reviews, May 27, 2010, vol. 39, pp. 3031-3056.

Zrazhevskiy, Paul et al., Designing multifunctional quantum dots for bioimaging, detection, and drug delivery, Chemical Society Reviews, Dec. 23, 2009, vol. 39, pp. 4326-4354.

Pinaud, Fabien et al., Probing cellular events, one quantum dot at a time, Nature Methods, Apr. 2010, vol. 7, No. 4, pp. 275-285.

Jaiswal, Jyoti K. et al., Long-term multiple color imaging of live cells using quantum dot bioconjugates, Nature Biotechnology, Jan. 2003, vol. 21, pp. 47-51.

Gao, Xiaohu, et al., In vivo cancer targeting and imaging with semiconductor quantum dots, Nature Biotechnology, Aug. 2004, vol. 22, No. 8, pp. 969-976.

Rossetti, R. et al., Size effects in the excited electronic states of small colloidal CdS crystallites, Journal of Chemical Physics, 1984, vol. 80, pp. 4464-4469.

Murray, C. B., et al., Synthesis and Characterization of Nearly Monodisperse CdE (E=S, Se, Te) Semiconductor Nanocrystallites, American Chemical Socity, 1993, vol. 115, pp. 8706-8715.

Dabbousi, B. O. et al., (CdSe)Zns Core-Shell Quantum Dots: Synthesis and Characterization of a Size Series of Highly Luminescent Nanocrystallites, 1997, vol. 101, pp. 9463-9475.

Liu, Wenhao et al., Compact Biocompatible Quantum Dots Functionalized for Cellular Imaging, Journal of American Chemical Society, 2008, vol. 130, pp. 1274-1284.

Susumu, Kimihiro et al., Multifunctional ligands based on dihydrolipoic acid and polyethylene glycol to promote biocompatibility of quantum dots, Nature Protocols, 2009, vol. 4, No. 3, pp. 424-436.

Jung, Jongjin et al., Selective Inhibition of Human Tumor Cells through Multifunctional Quantum-Dot-Based siRNA Delivery**, Angew. Chem. Inc. Ed., 2010, vol. 49, pp. 103-107.

Liu, Wenhao et al., Compact Biocompatible Quantum Dots via RAFT-Mediated Synthesis of Imidazole-Based Random Copolymer Lignad, American Chemical Society, 2010, vol. 132, pp. 472-483.

Lee, Jae-Hyun et al., Artificially engineered magnetic nanoparticles for ultra-sensitive molecular imaging, Jan. 2007, vol. 13, No. 1, pp. 95-99.

Stewart, Michael H. et al., Multidentate Poly(ethylene glycol) Ligands Provide Colloidal Stability to Semiconductor and Metallic Nanocrystals in Extreme Conditions, Journal of American Chemical Society, 2010, vol. 132, pp. 9804-9813.

Muro, Eleonora et al., Small and Stable Sulfobetaine Zwitterionic Quantum Dots for Functional Live-Cell Imaging, Journal of American Chemical Society, 2010, vol. 132, pp. 4556-4557.

Lees, Emma E. et al., Experimental Determination of Quantum Dot Size Distributions, Ligand Packing Densities, an Bioconjugation Using Analytical Ultracentrifugation, American Chemical Society, 2008, vol. 8, No. 9, pp. 2883-2890.

Liu, Lu et al., Bifunctional Multidentate Ligand Modified Highly Stable Water-Soluble Quantum Dots, Inorganic Chemistry, American Chemical Society, 2010, vol. 49, pp. 3768-3775.

Clapp, Aaron R. et al., Capping of CdSe—ZnS quantum dots with DHLA and subsequent conjugation with proteins, Nature Protocols, 2006, vol. 1, No. 3, pp. 1258-1266.

Qu, Lianhua et al., Alternative Routes toward High Quality CdSe Nanocrystals, American Chemical Society, 2001, vol. 1, No. 6, pp. 333-337.

Mei, Bing C., Modular poly(ethylene glycol) ligands for biocompatible semiconductor and gold nanocrystals with extended pH and ionic stability, J. Mater. Chem., 2008, vol. 18, pp. 4949-4958.

Uyeda, Tetsuo H. et al., Synthesis of Compact Multidentate Ligands to Prepare Stable Hydrophilic Quantum Dot Fluorophores, Journal of American Chemical Society, 2005, vol. 127, pp. 3870-3878.

Choi, Chung Hang J., et al., Mechanism of active targeting in solid tumors with transferrin-containing gold nanoparticles, PNAS, Jan. 19, 2010, vol. 107, No. 3, 1235-1240.

Clapp, Aaron R. et al., Fluorescence Resonance Energy Transfer Between Quantum Dot Donors, Journal of American Chemical Society, 2004, vol. 126, pp. 301-310.

Medintz, Igor L., et al., Proteolytic activity monitored by fluorescence resonance energy transfer through quantum-dot-peptide conjugates, Nature Materials, Jul. 2006, vol. 5, pp. 581-589.

Chen, Chun-Yen et al., Potassium ion recognition by 15-crown-5 functionalized CdSe/ZnS quantum dots in H2O, Chem. Commun, 2006, pp. 263-265.

Susumu, Kimihiro et al., Colloidal Quantum Dots: Synthesis, Photophysical Properties, and Biofunctionalization Strategies, Atrech House, Aug. 25, 2008, pp. 1-26.

Hines, Margaret A., et al., Synthesis and Characterization of Strongly Luminescing ZnS-Capped CdSe Nanocrystals, J. Phys. Chem, American Chemical Society, 1996, vol. 100, No. 2, pp. 468-471.

van Embden, Joel et al., Mapping the Optical Properties of CdSe/CdS Heterostructure Nanocrystals: The Effects of Core Size and Shell Thickness, Journal of American Chemical Society, 2009, vol. 131, pp. 14299-14309.

Gerion, Daniele et al., Synthesis and Properties of Biocompatible Water-Soluble Silica-Coated CdSe/ZnS Semicondutor Quantum Dots, J. Phys. Chem. B, 2001, vol. 105, pp. 8861-8871.

Bhang, Suk Ho et al., Hyaluronic Acid-Quantum Dot Conjugates for In Vivo Lymphatic Vessel Imaging, American Chemical Society, May 28, 2009, vol. 3, No. 6, pp. 1389-1398.

Yildiz, Ibrahim et al., Biocompatible CdSe—ZnS Core-Shell Quantum Dots Coated with Hydrophilic Polythiols, American Chemical Society, 2009, vol. 25, No. 12, pp. 7090-7096.

(56) References Cited

OTHER PUBLICATIONS

Yildiz, Ibrahim et al., Biocompatible CdSe—ZnS Core-Shell Quantum Dots with Reactive Function Groups on Their Surface, Langmuir, 2010, vol. 26, No. 13, pp. 11503-11511.

Shen, Hongyan et al., Poly(ethylene glycol) Carbondiimide Coupling Reagents for the Biological and Chemical Functionalization of Water-Soluble Nanoparticles, American Chemical Society, 2009, vol. 3, No. 4, pp. 915-923.

Anderson, Robin E. et al., Systematic Investigation of Preparing Biocompatible, Single, and Small ZnS-Capped CdSe Quantum Dots with Amphiphilic Polymers, American Chemical Society, 2008, vol. 2, No. 7, pp. 1341-1352.

Bullen, C. et al., The Effects of Chemisorption on the Luminescence of CdSe Quantum Dots, Langmuir, 2006, vol. 22, pp. 3007-3013.

Munro, Andrea M. et al., Quantitative Study of the Effects of Surface Ligand Concentration on CdSe Nanocrystal Photoluminescence, J. Phys. Chem. C, 2007, vol. 111, pp. 6220-6227.

Mei, Bing C. et al., Effects of Ligand Coordination Number and Surface Curvature on the Stability of Gold Nanoparticles in Aqueous Solutions, Langmuir, American Chemical Society, 2009, vol. 25, No. 18, pp. 10604-10611.

Na, Hyon Bin et al., Multidentate Catechol-Based Polyethylene Glycol Oligomers Provide Enhanced Stability and Biocompatibility to Iron Oxide Nanoparticles, American Chemical Society, 2012, vol. 6, No. 1, pp. 389-399.

\* cited by examiner

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence -continued

```
<220> FEATURE:
<223> OTHER INFORMATION: Synthetic Peptide

<400> SEQUENCE: 1

Cys Gly Asn Gly Ile Gln Val Arg Ile Lys Pro Gly Ser Ala Asn
1               5                   10                  15
```

POLYETHYLENE GLYCOL BASED OLIGOMERS FOR COATING NANOPARTICLES, NANOPARTICLES COATED THEREWITH, AND RELATED METHODS

CROSS-REFERENCE TO RELATED APPLICATIONS

This application is a divisional application of U.S. application Ser. No. 13/772,632, which was filed Feb. 21, 2014 and which is incorporated herein by reference as if set forth in its entirety. U.S. application Ser. No. 13/772,632 is a continuation-in-part of U.S. application Ser. No. 13/608,119 filed Sep. 10, 2012 and titled "Multidentate Polyethylene Glycol Based Oligomers, Nanoparticles Coated Therewith, and Related Methods," and which is incorporated herein by reference as if set forth in its entirety. U.S. application Ser. No. 13/608,119 claims the benefit of U.S. Provisional Application Ser. No. 61/532,756 filed Sep. 9, 2011 and titled "Ligands for Biocompatible Nanoparticles." All of the referenced applications are incorporated by reference as if set forth in their entireties.

STATEMENT REGARDING FEDERALLY SPONSORED RESEARCH OR DEVELOPMENT

This invention was made with Government support under Grant CHE-1058957 awarded by the National Science Foundation. The Government has certain rights in the invention.

FIELD OF THE INVENTION

This invention relates to the field of nanoparticle coatings. More particularly, the invention relates to bio-compatible nanoparticle coatings.

BACKGROUND

In the last two decades, a variety of inorganic nanocrystals have been designed, synthesized and characterized, with the ultimate goals of developing a fundamental understanding of some of their unique chemical, physical and optical properties while exploiting the potential they offer in applications ranging from electronic devises to biology.[1-7] Their properties often exhibit size and composition dependence, and are not shared by their bulk parent material or at the molecular scale.[4-7]

These unique and controllable properties have permitted researchers across different fields to overcome some of the limitations encountered by conventional (bulk and such) materials for expanding old and developing new technologies. Among these nanostructured materials, pure and metal-doped iron oxide nanocrystals constitute one of the most exciting platforms due to their size- and composition-dependent magnetic properties. They have generated a great of deal of interest for use as magnetic resonance imaging (MRI) contrast agents, in magnetic guidance and/or separation, and as biological platforms for intracellular imaging.[7-10]

In the early stage of development (late 1980s), large superparamagnetic iron oxide nanoparticles (SPIO, with dimensions >100 nm) containing several $Fe_3O_4$ nanocrystals were developed as in vivo $T_2$ MRI contrast agents.[9] More recently, and thanks to some remarkable improvements in the synthesis of high-quality nanocrystals using high temperature growth methods, preparation of several iron oxide-based nanocrystals, with demonstrated control over size- and composition-dependent magnetic properties have been reported.[11-13]

This control has intensified interest in further enhancing the contrast efficiency and understanding the biological distribution of these materials inside organisms.[13,14] However, issues of biological targeting, biodistribution and in vivo toxicity of nanomaterials, in general, greatly depend on their stability in complex biological media, their biocompatibility, and their hydrodynamic dimensions. These properties are directly controlled by one's ability to interface them effectively and reproducibly with biological systems.

Any nanoparticle platform with potential for use in biomedical applications should satisfy a few requirements, namely: 1) the surface coating of the nanoparticle should promote biocompatibility and reduce non-specific interactions while maintaining a compact size; 2) the nanoparticle should exhibit long-term stability in the presence of high electrolyte concentrations and over a broad pH range; and 3) the nanoparticles should have effective and controllable surface functionalization, which permits control over the number and nature of biomolecules attached to the nanoparticles, thus facilitating their use in applications such as targeting, sensing, and imaging.

The most effective synthetic strategies for obtaining high quality magnetic nanocrystals are based on a high temperature reaction of organometallic precursors. These strategies provide nanocrystals that are dispersible mainly in hydrophobic solutions, i.e., water-immiscible nanoparticles. Thus, additional processing using surface ligand exchange or encapsulation within phospholipid micelles or block copolymers is required to transfer these materials to buffer media and to impart biocompatibility. For instance, cap exchange with bifunctional hydrophilic ligands is simple to implement and can produce compact hydrophilic platforms.[13-18] Nonetheless, these strategies often rely on the use of commercially available but ineffective ligands or large mass block copolymers. These approaches provide nanoparticles with limited long term stability and/or substantially increased hydrodynamic size.

It has been demonstrated that catechol derivatives such as the neurotransmitter dopamine and L-3,4-dihydroxyphenyl-alanine (L-DOPA), a precursor to dopamine that is also used as a component of adhesives generated by marine mussels, exhibit strong affinity to metal oxide nanocrystals.[16,19,20] Several recent studies have reported that catechol-appended single chain PEGs provide effective capping ligands for iron oxide nanocrystals and permit their transfer to aqueous media. Catechol-PEG-capped iron oxide nanoparticles also have been used in cellular labeling and targeted MR imaging studies[17,18,21-23].

Although these coating polymers are water dispersible, improvement is needed.

SUMMARY

We have developed nanoparticle coatings that are water dispersible, have a strong affinity for binding to magnetic nanoparticles, and can be easily modified for attaching the coating to biological materials. The nanoparticle coatings comprise a polyacrylic acid based backbone onto which PEG-based oligomers are appended by modifying the native carboxyl groups of the PAA backbone. The PEG-based oligomers include functional groups on their terminal ends, which are chosen to provide a certain function. Some of the terminal functional groups bind the coatings to the nanoparticle's surface, while others provide reactive sites for binding other compounds to the coating. The method we developed for making these coatings allows one to tune the number and type of PEG-based oligomers appended to the PAA backbone based on the desired properties of the coating.

In accordance with a composition aspect of the invention, the nanoparticle coatings comprise repeating polyacrylic acid monomers covalently bound together in an aliphatic chain having a plurality of carboxylic acid functional groups and modified carboxylic acid functional groups extending therefrom. A first portion of the modified carboxylic acid functional groups are modified by a PEG oligomer having a terminal methoxy functional group and a second portion of the modified carboxylic acid functional groups are modified by a PEG oligomer having at least one terminal catechol group.

These and other aspects, embodiments, and features of the invention will be better understood in the context of the accompanying drawings and the following Detailed Description of Preferred Embodiments.

DETAILED DESCRIPTION OF PREFERRED EMBODIMENTS

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will convey preferred embodiments of the invention to those skilled in the art.

The inventors have developed new set of PEG-based oligomer nanoparticle coating ligands that have increased coordination to magnetic nanoparticle surfaces, affinity to aqueous media, and the ability to be conjugated to biomolecules. For this, the inventors have used PAA as a central backbone onto which PEG-based oligomers are bound using a simple approach based on N,N-dicyclohexylcarbodiimide (DCC) coupling. These PEG-based oligomers can be used for coating magnetic nanoparticles such as those comprising iron oxide The process for making these PEG-based oligomer coatings, also developed by the inventors, allows specific functional groups such as azides, amines, and catechols to be incorporated into the coating. These PEG-based oligomer coatings exhibit one or more of the following advantageous features: (i) they include multiple nanoparticle anchoring groups bound to a single PAA oligomer, (ii) they include multiple PEG oligomers bound to a single PAA oligomer, and (iii) the number of reactive functional groups incorporated into the coating is tunable.

Figure 1:
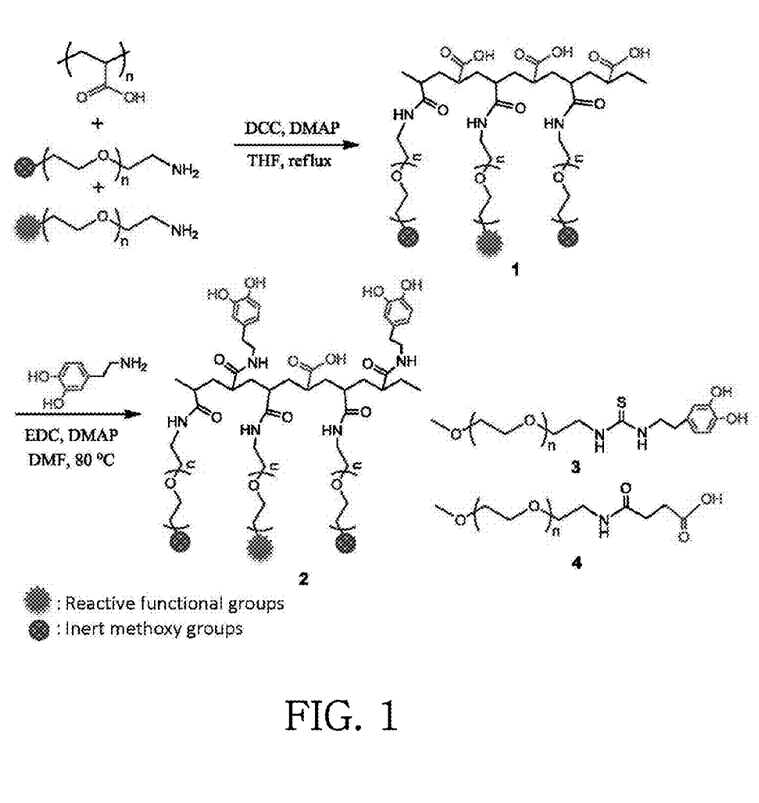
FIG. 1 is a schematic diagram of the chemical structures and synthetic strategy of making nanoparticle coatings in accordance with an embodiment of the invention. The top panel shows a preferred process for making Compound 1. The bottom left panel shows a preferred process for making Compound 2. The bottom right panel shows the structures of mono-PEG-Dopa (Compound 3) and mono-PEG-COOH (Compound 4).

A first composition aspect of the invention is now described with reference to FIG. 1. In FIG. 1, several of the preferred PEG oligomers and nanoparticle coatings are shown. For ease of reference, each is assigned a corresponding compound number, which appears below the compound's molecular diagram. The abbreviations used are summarized in Table 1.

In a preferred embodiment of the first composition aspect of the invention, the PEG-based nanoparticle coating is composed of repeating polyacrylic acid monomer units covalently bound together to form an aliphatic chain having a plurality of carboxylic acid functional groups and modified carboxylic acid functional groups extending therefrom. The number of polyacrylic acid monomer units is preferably between about 20 to about 30. More preferably, the number of polyacrylic acid monomer units is about 25.

The modified carboxylic acid functional groups are functional groups formed by modifying a portion of the native carboxylic acid groups on polyacrylic acid monomer units. Preferably, the modified carboxylic acid functional groups include amide groups formed from the combination of the aliphatic PAA chain with aminated PEG-based olgomers.

A first portion of the modified carboxylic acid functional groups are modified by a PEG oligomer having a terminal methoxy functional group such as —NH-PEG-OCH$_3$. A preferred average molecular weight for the PEG section of this oligomer is about 750 (PEG 750). The terminal methoxy functional groups are advantageous because they are generally not reactive with the surface of nanoparticles or bio-molecules.

A second portion of the modified carboxylic acid functional groups are modified by a functional group having a terminal catechol moiety. Because the terminal catechol moiety(ies) bound to the surface of iron oxide nanoparticles, they are effective at anchoring the nanoparticle coating to the surface of the nanoparticle. Preferred catechol moieties are formed from catechol moieties including, but not limited to —NH—R-catechol and dopamine. Here R represents an alkane, alkene, or alkyne.

Optionally, a third portion of the modified carboxylic acid functional groups are modified by a PEG oligomer having a terminal functional group that includes a terminal amine or azide moiety such as —NH-PEG-N$_3$. A preferred average molecular weight for the PEG section of this oligomer is about 600 (PEG 600). compound 2, shown in FIG. 1 provides a representative example of nanoparticle coating having a PAA backbone having carboxylic acid groups modified with —NH-PEG-OCH$_3$, —NH—R-catechol, and —NH-PEG-N$_3$.

In a second composition aspect of the invention, magnetic nanoparticles are coated with one or more of the nanoparticle coatings described above. The nanoparticles are preferably made of iron oxide or another material to which catechols will bind. The nanoparticles are coated by being directly bound to the terminal catechol moieties.

A preferred method of making multidentate polyethylene glycol (PEG)-based oligomer nanoparticle coatings, in accordance with a method aspect of the invention, is now described.

The nanoparticle coating compositions described above are formed using Oligo-PEG-COOH precursors such as compound 1 and compound 1-1 for example.

A first Oligo-PEG-COOH precursor is synthesized by cooling a first solution of PAA and a solvent to a first temperature. Preferably, the first temperature is approximately −5° C. to approximately 5° C., or, more preferably, about 0° C. The solvent is preferably a polar aprotic organic solvent such as THF or the like. DCC is then blended with the first solution to form a second solution. DMAP and the PEG oligomer having a terminal methoxy functional group are added to the second solution. The first Oligo-PEG-COOH precursor is then removed from the reaction mixture. Compound 1 is an example of the first precursor.

A second Oligo-PEG-COOH precursor is synthesized by cooling a first solution of PAA and a solvent to a first temperature. Preferably, the first temperature is approximately −5° C. to approximately 5° C., or, more preferably, about 0° C. The solvent is preferably a polar aprotic organic solvent such as THF or the like. DCC is then blended with the first solution to form a second solution. DMAP, the PEG oligomer having a terminal methoxy functional group and a PEG oligomer having a terminal azide group are added to the second solution. The second Oligo-PEG-COOH precursor is then removed from the reaction mixture. Compound 1-1 is an example of the second precursor.

A preferred method of synthesizing a nanoparticle coating using either of these precursors involves preparing a first solution of EDC, DMF, and triethylamine, then adding the desired precursor to the first solution. The catechol and DMAP are added to the first solution to form a second solution. The second solution is heated to between about 70° C. to about 90° C. The reaction product is then purified and removed from the reaction mixture and reduced with a reducing agent such as hydrazine or the like. The reduced reaction product is the nanoparticle coating.

A particularly advantageous feature of this method is the fact that the number of terminal catechol moieties, terminal methoxy groups, and azide groups attached along the PAA chain can be engineered as desired by changing the amount of each relative to the number of carboxyl groups along the native PAA chain in the synthesis process.

EXAMPLES

The embodiments of the invention described above will be even better understood in the context of the following examples. These examples are not intended to limit the scope of the invention in any way.

We have developed multidentate nanoparticle coating ligands with strong affinity to iron oxide nanocrystals using a short PAA (Mw~1800 or an index of polymerization of ~25) as the platform/backbone to graft multiple anchoring groups along with multiple PEG moieties within the same structure. This design provides a small coating with a relatively low molecular weight and accommodates several anchoring groups and several PEG moieties within the same structure.

We describe the use of these nanoparticle coatings to cap iron oxide nanoparticles and transfer them to buffer media. Our ligands were prepared by laterally grafting several PEG moieties and several catechol groups onto a polyacrylic acid short chain. In this design, the intrinsic ligand structure, including the density of anchoring groups, the size of PEG, and the type of end reactive groups can be controlled, all while maintaining a compact size. Cap exchange with these oligomers was rapid and provided iron oxide NPs that are stable for at least 60 days in the presence of large excess of added salts and over a broad range of pHs, from pH 4 to pH 11. Colloidal stability is vastly improved compared to other lower coordination ligands such as mono-PEG-catechol or oligomers presenting weaker coordinating COOH groups.

We also showed that controllable fractions of azides can be introduced into the oligomer ligand, producing NPs that are reactive with complementary functionalities. In particular, we demonstrated the ability to couple azide-functionalized NPs to an alkyne-modified dye, which opens up the possibility of biological targeting of these NPs. We also measured the MRI contrast properties of these OligoPEG-capped Fe$_3$O$_4$ nanoparticles and found that they exhibit strong T2 contrast enhancement with dependence on size of the nanocrystals.

Preliminary MTT assay using these OligoPEG-NPs indicated no measurable toxicity of the NPs to live cells. We believe that this approach can be expanded to prepare other types of functionalized oligomers with tailor-designed anchoring groups and reactive groups, which will allow the hydrophilic transfer and coupling of a variety of inorganic nanocrystals.

We tested nanoparticle coatings with two types of anchoring groups: (1) the native carboxyl groups present on the polyacrylic acid oligomer (compound 1) and (2) several dopamines and amine-terminated PEGs were grafted onto the PAA, producing an oligomer that presents several catechol anchoring groups together with multiple PEG moieties (compound 2). We also prepared and tested two molecular scale PEG-appended ligands, a mono-PEG-Dopa (compound 3) and a mono-PEG-COOH (compound 4). Here we used compounds 1, 3, and 4 as control ligands to which the data on compounds 2 and 2-1 were compared. This allowed us to test the effects of coordination number as well as the nature of the anchoring group used on the cap exchange and on the quality of the resulting $Fe_3O_4$ nanoparticles.

Figure 2A:
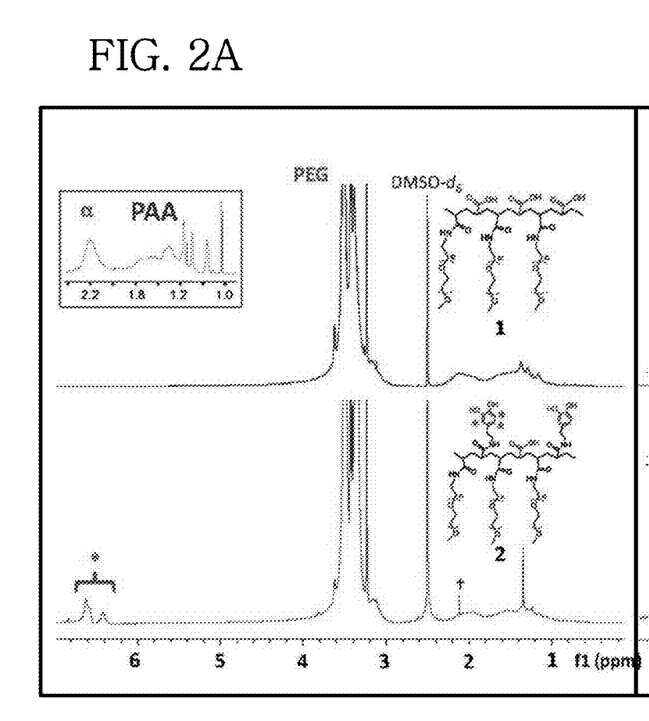
FIG. 2A shows $^1$H NMR spectra of Compounds 1 and 2 measured in DMSO-d6. The signature of PEG around 3.26-3.64 ppm and the singlet peak from the protons of methoxy at 3.23 ppm are dominant in spectra. Multiplet peaks around 1.86-2.23 ppm ($\alpha$) and at 6.32-6.78 ppm (*) were ascribed to the $\alpha$-hydrogens of PAA and the protons in the catechols, respectively. The Inset shows a $^1$H NMR spectrum of PAA.

FIG. 1 provides a schematic depiction of the synthetic steps involved in the preparation of the carboxyl- and catechol-PEG-derivatized oligomers. We used commercial PAA, along with molecular scale bifunctional PEG moieties, which we have described in previous reports.[25,26] For the OligoPEG-COOH ligand (compound 1) a fraction of the carboxylic acids along the PAA backbone was reacted (via DCC coupling in THF) with $NH_2$-PEG-$OCH_3$. Characterization of the oligomer ligand using $^1$H NMR spectroscopy (in DMSO-d6) showed that multiple PEG moieties were indeed coupled to the PAA, as indicated by the appearance of a new strong broad peak at 3.26-3.64 ppm (attributed to PEG segments) and a second sharp peak at 3.23 ppm attributed to $OCH_3$ groups; the weak broad peaks at 1.1-2.3 ppm are ascribed to PAA (FIG. 2a). We should note that the exact location of these peaks depends on the solvent used. For example, a peak at 3.38 ppm was measured for this methoxy group in $CDCl_3$.[25] FT-IR analysis further confirmed the presence of amide bonds linking the PEG moieties to PAA with bands at 1645 $cm^{-1}$ and 1531 $cm^{-1}$. In a typical experiment, the degree of grafting was estimated from the $^1$H NMR spectrum by comparing the relative integrations of the α-hydrogen peak from the acrylic acid repeat units of PAA (δ=1.86-2.23, 25H) and the three protons in the lateral methoxy group of PEG-$OCH_3$ (δ=3.23, 38.8H); we measured ~13 PEG moieties per PAA chain.

Synthesis of Azide Functionalized OligoPEG-COOH (Compound 1-1).

Figure 2B:
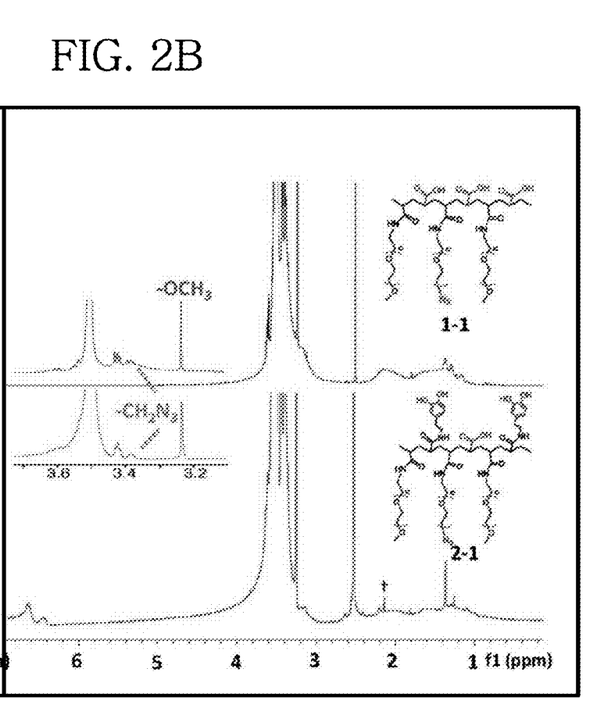
FIG. 2B shows $^1$H NMR spectra of Compounds 1-1 and 2-1 measured in DMSO-d6. The signature of azide (—$CH_2N_3$) at 3.39 ppm and the singlet peak from the protons of methoxy at 3.23 ppm are present in both spectra (inset). The peak signatures of PEG, the $\alpha$-hydrogens of PAA, and the protons in the catechols are identical. The peak in the spectra at 2.1 ppm, marked by †, is attributed to acetone.

To prepare azide-functionalized OligoPEG-COOH (e.g., compound 1-1), a mixture of $OCH_3$— and $N_3$-terminated PEG-$NH_2$ moieties was used during the DCC coupling reaction. By varying the relative amounts (fractions) of azide-PEG and $H_3CO$-PEG moieties, one can control the number of azide groups per oligomer. Here, we prepared and characterized of an azide-functionalized OligoPEG-COOH with a nominal azide-to-methoxy ratio of 1:3 (or 25% azide-PEG). The azide signature manifests as a triplet peak at 3.39 ppm in the $^1$H NMR spectrum; additionally, a new vibration band at 2108 $cm^{-1}$ is measured in the FT-IR spectrum (FIG. 2b).

For the OligoPEG-Dopa ligands (compounds 2 and 2-1), the synthesis was carried out in two steps: 1) First a fraction of the carboxyl groups along the PAA backbone was reacted (via DCC in the presence of DMAP in THF) with either $NH_2$-PEG-$OCH_3$ or a mixture of $NH_2$-$PEGOCH_3$ and $NH_2$-PEG-$N_3$, as discussed above for the OligoPEG-COOH (compound 1 and 1-1). 2) After purification, the rest of the carboxyl groups along the PEGylated oligomer intermediate were reacted (via EDC condensation) with dopamine. We found that the use of EDC condensation (instead of DCC) allowed not only a more efficient coupling between the carboxylic acids along the PAA (OligoPEG-COOH) and dopamine, but also facile removal of the byproducts and unreacted precursors by dialysis. $^1$H NMR analysis confirmed that catechol groups, PEG moieties and methoxy groups are present in the oligomer. In particular, a multiplet at 6.32-6.78 ppm (catechol protons), a strong peak at 3.26-3.64 ppm (due to PEG) and a sharp peak at 3.23 ppm (due to methoxy) were measured in the NMR spectra (see FIG. 2). The degree of grafting was estimated to be 6.2 catechols per chain (or oligomer), derived from comparing the relative integrations of the 25 α-hydrogens from the acrylic acid repeat unit of PAA (δ=1.86-2.23, 25H) and the three protons per catechol (δ=6.32-6.78, 18.5H total). In addition, FT-IR data analysis of the OligoPEG-Dopa (compound 2) showed a sizable decrease in the signature of carboxyl groups at 1722 $cm^{-1}$, which provides further inference that catechol groups have been grafted onto the PAA backbone during this reaction step.

Additional, though indirect, proof for the presence of catechol groups in the OligoPEG-Dopa ligand structure relied on UV-Vis absorption, for which a clear pH-dependent change in the absorption spectra of compound 2 was measured. In particular, we measured a progressive increase coupled with broadening of the peak at 280 nm for solution of compound 2 as the pH of the solution was increased. The most pronounced changes were measured at pH ≥9, with equilibrium usually reached after 90 minutes. This change in absorption is similar to that measured for the mono-PEG-Dopa ligand (compound 3). This change is a characteristic signature of the catechol group in the presence of oxygen when the solution pH is increased.

Figure 3:
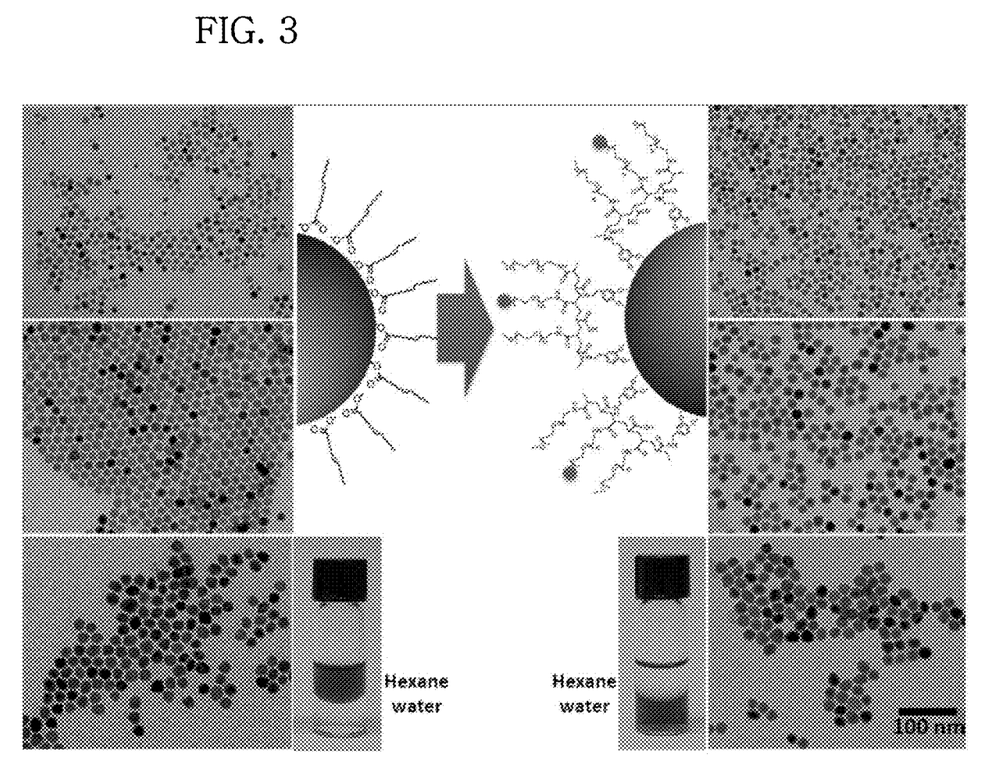
FIG. 3 shows TEM images of $Fe_3O_4$ NPs with 11, 17 and 23 nm core size before (left) and after (right) ligand exchange with Compound 2 and a schematic representation of the NP with the corresponding surface cap along with images of the organic and aqueous dispersions.

We found that ligand exchange of $Fe_3O_4$ nanoparticles (capped with the native oleic acid) can be carried out using three sets of ligands, namely mono-PEG-Dopa, OligoPEG-COOH and OligoPEG-Dopa. However, we observed substantial differences between the various ligands in the ease of implementing the cap exchange procedure and in the long term stability to changes in pH and to added electrolytes. While cap exchange with the OligoPEG-Dopa and even the monoPEG-Dopa was rapid and required only incubation at room temperature, cap exchange with OligoPEG-COOH ligand required heating at ~70° C. In comparison, mono-PEG-COOH (compound 4) could not stabilize iron oxide NPs even with longer incubation times and heating to ~70° C. This reflects the inherent weak coordination of a single COOH group (compared to a single catechol) to iron oxide surfaces. TEM images of nanoparticles cap exchanged with OligoPEG-Dopa (compound 2), shown in FIG. 3, indicate that the integrity of the nanoparticles was conserved, with no change in the overall size or shape; this confirms that the new ligands did not induce any damage or leaching of metal ions off the nanoparticle surfaces.

Figure 4A:
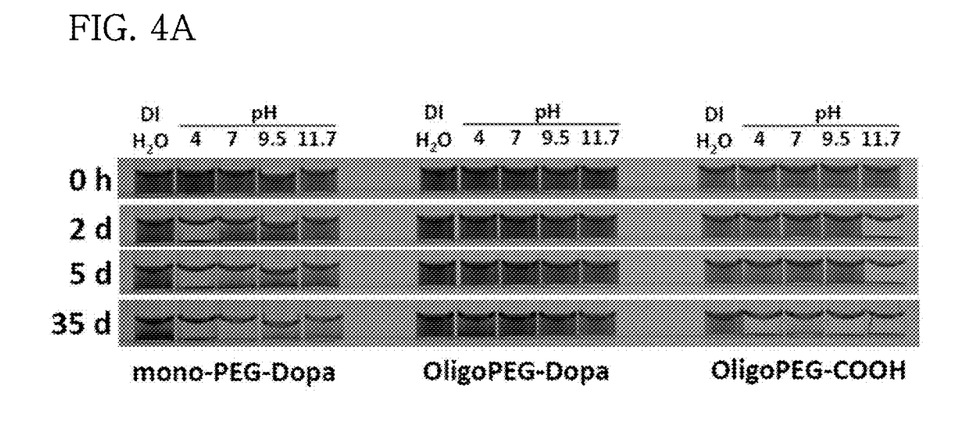
FIG. 4A shows stability testing data of $Fe_3O_4$ NP dispersion in various pH buffers. Shown are Mono-PEG-Dopa-stabilized (compound 3) NPs (left), OligoPEG-Dopa-stabilized (Compound 2) NPs (middle), and OligoPEG-COOH-stabilized (Compound 1) NPs (right).
Figure 4B:
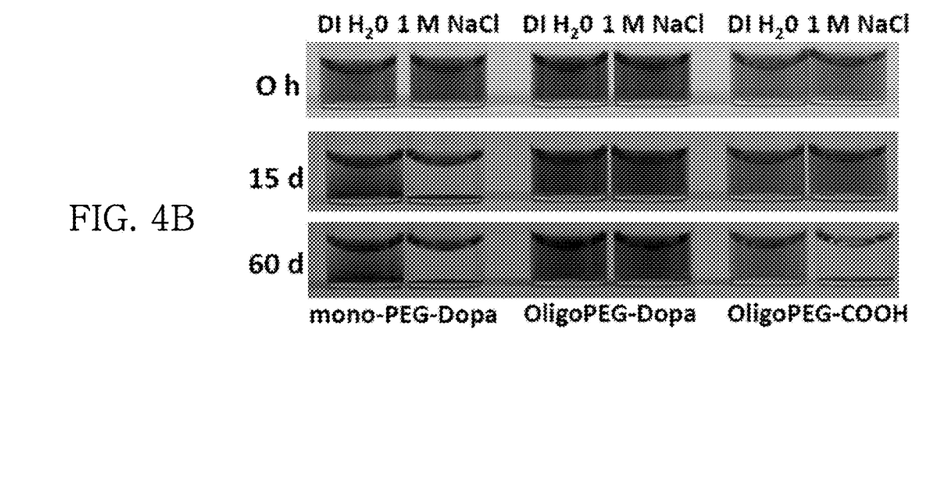
FIG. 4B shows stability testing data of $Fe_3O_4$ NP dispersion in 1 M NaCl. Shown are Mono-PEG-Dopa-NPs (Compound 3) (left), OligoPEG-Dopa-NPs (Compound 2) (middle), and OligoPEG-COOH-NPs (Compound 1) (right).

Side-by-side comparison of the stability of iron oxide NPs capped with the PEGylated oligomers to pH changes showed that while both compounds provided dispersions that were stable over the short term, only the OligoPEG-Dopa provided well dispersed NPs over the full range of pHs. For instance, OligoPEG-COOH-NPs slowly became turbid and precipitated after ~5 weeks of storage, but at pH 11 or higher precipitation occurred after one day. Conversely, NPs cap-exchanged with mono-PEG-Dopa exhibited limited stability, as precipitation took place after 1 day at pH 4 and after 35 days at basic pH 11 or higher (see FIG. 4a). Stability of NP dispersions to excess electrolytes (namely 1 M NaCl) exhibited a similar trend. The images shown in FIG. 4b indicate that OligoPEG-Dopa ligand produces more stable NP dispersions than OligoPEG-COOH and mono-PEG-Dopa, as NPs capped with compound 1 precipitated after 1 month of storage and those capped with compound 3 precipitated after 10 days. In comparison, NP capped with compound 2 stayed stable for at least 2 months. When dispersed in DI water, NPs capped with compound 2 stayed stable for longer times, at least six months.

Cumulatively, these tests confirm that individually a catechol group exhibits much stronger affinity to iron oxide than a carboxyl group, though long term stability provided by both ligands is poor. They also clearly prove that ligands presenting multiple carboxyl groups or multiple catechols exhibit enhanced binding to the nanoparticle surface; sizable differences between the two types of oligomers exist nonetheless. In particular, we found that the multi-catechol presenting ligand (compound 2) imparts the highest stability against changes in the solution pH and to added NaCl. This supports prior findings for which the benefits of multi-coordinating ligands and their ability to impart better colloidal stability to Au NPs and QDs (due to enhanced binding affinity), has been documented by us and others.[24,25,27] However, reports on the hydrophilic stabilization of metal oxide NPs (such $Fe_3O_4$) were rather limited.[13,21,24,28] The most promising results were obtained mainly via encapsulation within large molecular weight block copolymers or silica shell, albeit with the sizable increase in the NP hydrodynamic size.[29-31]

Our nanoparticle coatings offer a promising platform for substantially improving the stability of such magnetic nanoparticles in variety of biologically relevant conditions, including acidic, basic, and electrolyte- and protein-rich media.

We carried three additional and independent tests on the new set of nanoparticles with direct implications in biology.

We first tested the ability to conjugate the newly designed OligoPEG-NPs to alkyne-modified fluorescent dye using copper(I) catalyzed azide-alkyne cycloaddition (CuAAC or Click) reaction. $Fe_3O_4$ NPs cap-exchanged with compound 2-1 were designed to present a few azide-terminated PEG moieties on their surfaces, making them potentially compatible with Click reaction. Azide-alkyne cycloaddition as a coupling strategy has generated a tremendous interest and activity, because of its efficiency, high chemoselectivity, and reduced cross reactivity.[32-35] It is also compatible with a wide range of solvents and pHs. Click offers a good alternative to other more conventional reaction schemes that often rely on the reactivity of amide, ester or thioether with naturally abundant carboxyl, amine and thiol groups. Their abundance, however, can induce high levels of nonspecific and unintended conjugation of proteins and peptides.[35-37]

Figures 5A, 5B:
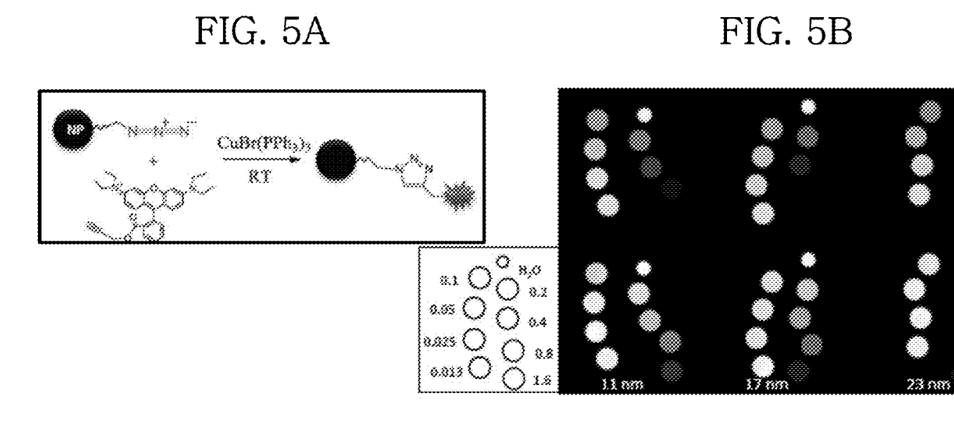
FIG. 5A shows fluorescent dye conjugation and MR imaging data of CuAAC conjugation of alkyne-functionalized dyes to azide-functionalized iron oxide NPs.
FIG. 5B shows absorption (black) and fluorescence (red) spectra after rhodamine B conjugation of azide-functionalized OligoPEG-Dopa-NPs. The Inset shows the deconvoluted spectrum of rhodamine B.

To demonstrate the compatibility of our azide-functionalized OligoPEG-Dopa-NPs with this coupling route, we reacted the NPs with an alkyne-modified rhodamine B dye (see scheme in FIG. 5a). The dye-conjugated NPs were characterized using absorption and fluorescence measurements. FIG. 5b shows the absorption and fluorescence spectra of the dye-reacted NP dispersions following purification. Both spectra indicate the presence of bound rhodamine B onto the NPs. In particular, there is an additional absorption peak at ~566 nm and a pronounced fluorescence signal characteristic of the rhodamine B dye at 577 nm; the deconvoluted dye contribution to the absorption spectrum is shown in the insert in FIG. 5b. These optical signatures are characteristic of the rhodamine B dye, clearly confirming that Click-driven coupling between the azide-functionalized NPs and alkyne-rhodamine B has taken place. The absorption and fluorescence peaks of the NP-attached dye exhibit a small red shift compared to the dye alone; such shifts are often observed when dyes are attached to proteins and peptides.

From the absorption data and using the extinction coefficient for rhodamine B (87,000 $M^{-1}cm^{-1}$ at 554 nm, peak), we estimate that there are ~82 dyes per $Fe_3O_4$ nanoparticle. Though preliminary, this result clearly proves the potentials of our ligand design applied to magnetic NPs and could allow for developing a multimodal-imaging agent based on MR contrast.

Figure 5C:
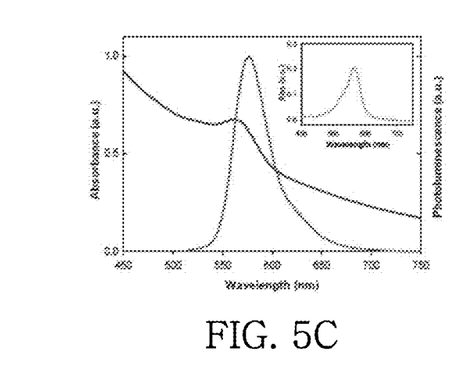
FIG. 5C shows the T2-weighted spin-echo images (TE/TR=16/5000 ms) of the different size nanoparticles with increased dilutions as shown in the inset (top) and T2* weighted gradient recalled echo images (TE/TR=3/5000 ms) (bottom). The corresponding iron concentrations (in mM) in each capsule are shown in the sketch.

In the second test, we evaluated the MRI contrast signature of $Fe_3O_4$ NPs capped with OligoPEG-Dopa ligands; (iron oxide NPs have been tested as efficient T2 MRI contrast agents). Three different size NPs (11, 17, and 23 nm diameter as estimated from TEM) stabilized with compound 2 were prepared and dispersed in buffer solutions. T1, T2 and T2* signals were collected and used to extract estimates for r1, r2 and r2* relaxivities. FIG. 5c shows the T2weighted spin-echo images of the different NPs with varying dilutions, along with the corresponding T2*-weighted gradients. A strong enhancement in the T2 and T2* contrast signals with nanoparticle concentration and size was measured. We also measured a consistent trend in the size dependence of relaxivity, with r2=181, 234, and 254 $mM^{-1}s^{-1}$ for 11, 17, and 23 nm NPs, respectively.

Advantageously, the measured relaxivity r2 values for our hydrophilic $Fe_3O_4$ NPs are well in excess of those reported for commercial clinical agents. For example, some of the highest values reported for those agents (B0=0.47 T) are Feridex/Endorem (r2=160 $mM^{-1}s^{-1}$), Resovist (r2=151 $mM^{-1}s^{-1}$) and Sinerem (r2=160 $mM^{-1}s^{-1}$).[38,39]

Stability, biocompatibility and reduced interference with the biological functions of cells and animal functions of these magnetic nanoprobes is critical for use in applications, such as in vitro and in vivo imaging and sensing. Our OligoPEGs present a high number of biocompatible PEG moieties, which makes highly suitable for biological environments. We assessed the cytotoxicity of the OligoPEG-Dopa-stabilized $Fe_3O_4$ nanoparticles (11 nm size) using MTT (3-(4,5-dimethylthiazol-2-yl)-2,5-diphenyltetrazolium bromide) assay on a rat microglia cell line (Bv2). The final concentration of $Fe_3O_4$ nanoparticles in the cell media was varied between 0.0625 and 2 mM (of equivalent Fe).

Figure 5D:
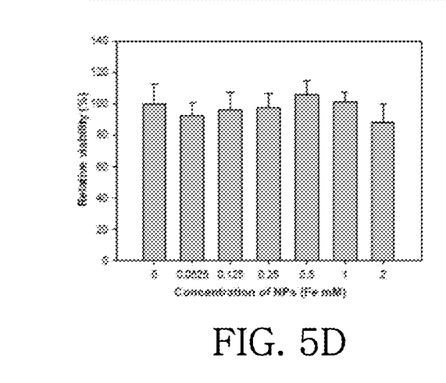
FIG. 5D shows a plot of the relative viability of Bv2 cells for increasing concentration of OligoPEG-Dopa-stabilized $Fe_3O_4$ nanoparticles performed using an MTT assay.

FIG. 5d shows that cell viability was largely unaffected by the presence of the NPs. The MTT assay proves that the present set of nanoparticles essentially has no measurable toxicity to the cells, further supporting our rationale that these multidentate PEG-rich oligomers should provide added biological compatibility to the magnetic nanoparticles, thus enhancing their potential utility in biomedical applications.

Synthesis of OligoPEG-COOH (Compound 1).

4.0 g of poly acrylic acid (PAA, MW=1800, 2.22 mmol) was dispersed in 100 mL of tetrahydrofuran (THF) in a 250 mL round bottom flask and cooled to 0° C. using an ice-bath with stirring. 4.59 g of N,N'-dicyclohexylcarbodiimide (DCC, 22.22 mmol) was added and the mixture was stirred for 30 min under N2. Then, 0.54 g of 4-(N,N-dimethylamino)pyridine (DMAP, 4.44 mmol) and 16.34 g of $H_2N$-PEG750-$OCH_3$ (22.22 mmol) were added, and the mixture was left refluxing for 2 days at ~70° C. The reaction mixture was filtered using a filter funnel and the solvent evaporated. 100 mL of deionized water containing 4 g of KOH were added to the residue, and the mixture was left stirring overnight, filtered, washed with ethyl acetate, and acidified using 1 N HCl solution to a pH 4. Chloroform was added to the aqueous solution to extract the product (3 times 100 mL each). The organic layers were combined dried over $Na_2SO_4$, filtered and the solvent evaporated under vacuum to yield the crude product, which was further purified using silica gel column chromatography using chloroform as the eluent.

Synthesis of Azide-Functionalized OligoPEG-COOH (Compound 1-1).

In a 250 mL round bottom flask 2.0 g of PAA (MW 1800, 1.11 mmol) were dispersed in 50 mL of THF and cooled to 0° C. using an ice-bath with stirring. 2.29 g of DCC (11.11 mmol) were added and the mixture was stirred for 30 min under $N_2$. 0.27 g of DMAP (2.22 mmol), 6.13 g of $H_2N$-PEG750-$OCH_3$ (8.33 mmol), and 1.73 g of $H_2N$-PEG600-$N_3$ (2.78 mmol) were added and the mixture left refluxing at ~70° C. for 2 days. The reaction mixture was filtered, the solvent was evaporated, then 100 mL of deionized water mixed with 2 g of KOH were added to the residue. After overnight stirring, the mixture was filtered then washed with ethyl acetate. The aqueous phase was acidified using 1N HCl to a pH 4, and the product was extracted with chloroform (3 times 100 mL each). The combined organic layer was dried over Na2SO4, filtered and the solvent evaporated. The product was further purified by silica gel column chromatography using chloroform as the eluent.

Synthesis of OligoPEG-Dopa (Compound 2).

In a 100 mL round bottom flask 320 mg of N-(3-dimethylaminopropyl)-N'-ethylcarbodiimide hydrochloride (EDC, 1.67 mmol) were dispersed in 10 mL of dimethylformamide (DMF) with equivalent molar amount of triethylamine. 1 g of compound 1 (OligoPEG-COOH, 0.11 mmol) was added and the mixture was cooled to 0° C. using an ice-bath with stirring. In a separate round bottom flask (50 mL), 475 mg of dopamine hydrochloride (2.50 mmol) was dispersed in 10 mL of dimethylformamide (DMF) with equivalent molar amount of triethylamine and stirred for 30 min at room temperature, then 41 mg of DMAP (0.33 mmol) were added. This dopamine solution was added to the solution containing compound 1, and the mixture was heated to 80° C. and left stirring for 5 days. After evaporating the solvent, 20 mL of deionized water containing 1 g of KOH were added to the flask, and the mixture was stirred overnight. The mixture was filtered, washed with ethyl acetate, and after neutralization by the addition of 1 N HCl, the mixture was dialyzed using a cellulose ester membrane with MW Cut-off of 1000 Da. The product was reduced with 1% hydrazine in deionized water, further purified via 2 round of dialysis, and then lyophilized.

Synthesis of Azide-Functionalized OligoPEG-Dopa (Compound 2-1).

218 mg of EDC (1.14 mmol) was dispersed in 5 mL of DMF with equivalent molar amount of triethylamine in a 100 mL round bottom flask. 0.66 g of azide-functionalized OligoPEG-COOH (compound 1-1, 0.08 mmol) was added and the mixture was cooled down to 0° C. using an ice-bath while stirring. In a separate vial 324 mg of dopamine hydrochloride (1.71 mmol) dispersed in 5 mL of DMF with equivalent molar amount of triethylamine and the mixture was stirred at room temperature. After 30 min, the dopamine solution and 28 mg of DMAP (0.23 mmol) were added to the solution containing EDC and compound 1-1. The mixture was left stirring at 80° C. for 5 days. After evaporating solvent, 10 mL of deionized water containing 0.66 g of KOH were added to the residue and stirred overnight. The solution mixture was filtered and washed with ethyl acetate. After neutralization by addition of 1 N HCl solution, the product was purified by dialysis using cellulose ester membrane (MW Cut-off=1000 Da). The product was reduced with 1% hydrazine in deionized water, further purified by dialysis, and lyophilized.

Cap Exchange of Iron Oxide Nanoparticles.

The iron oxide NPs were synthesized using thermal decomposition of Fe-oleate in high-boiling-point solvents, characterized and processed using procedures developed by Hyeon and co-workers.[12] Here, we describe the procedure used for capping $Fe_3O_4$ nanoparticles with compound 2 (OligoPEG-Dopa). 5 mg of iron oxide NPs with varying sizes (11, 17, and 23 nm) dispersed in 0.5 mL of THF were mixed with 25 mg of OligoPEG-Dopa, initially dissolved in 1 mL of ethanol, and stirred overnight at room temperature. The mixture was stirred overnight and resulted in a clear solution. The sample was then precipitated using hexane and centrifuged to provide a dark pellet of NPs. The dark pellet was readily dispersed in water, providing a clear solution. The aqueous dispersion was filtered through a 0.2 μm disposable syringe filter (Millipore), then excess free ligands and solubilized oleic acid were removed using 2 to 3 rounds of filtrations with deionized water (2-3 times) using a centrifugal filtration device (Millipore, Mw Cut-off: 100 kDa). Cap exchange with mono-PEG-Dopa followed the same steps as those employed with compound 2. The cap exchange with OligoPEG-COOH ligand (compound 1), followed the same procedure, except that the NP/ligand mixture in THF and ethanol required a slight heating to ~70° C. and incubation for longer times. Similar steps were employed for capping the NPs with mono-PEG-COOH.

Dye Conjugation Via Copper(I) Catalyzed Azide-Alkyne Cycloaddition.

The alkyne modified rhodamine B (RhB-alk) was synthesized via EDC coupling between rhodamine B and propargyl alcohol following the procedure described in reference.[40] Briefly, 30 μL of RhB-alk solution (2 mg/ml in DMSO) was mixed with 300 μL of azide-functionalized OligoPEG-Dopa-NPs dispersion (400 nM) in the presence of CuBr $(PPh_3)_3$ and stirred for 1 day at room temperature. After purification by the size exclusion using a PD10 column (GE healthcare) with DI water and the filtration through a 0.4 μm disposable syringe filter (Millipore), the eluted solution was characterized using absorption and fluorescence measurements.

The invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

REFERENCES

The following references are all incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

(1) Murray, C. B.; Kagan, C. R.; Bawendi, M. G. *Annu. Rev. Mater. Sci.* 2000, 30, 545.
(2) Park, J.; Joo, J.; Kwon, S. G.; Jang, Y.; Hyeon, T. *Angew. Chem., Int. Ed.* 2007, 46, 4630.
(3) Kwon, S. G.; Hyeon, T. *Acc. Chem. Res.* 2008, 41, 1696.
(4) Klabunde, K. J.; Richards, R. *Nanoscale materials in chemistry*; 2nd ed.; Wiley: Hoboken, N. J., 2009.
(5) Mattoussi, H.; Cheon, J. *Inorganic nanoprobes for biological sensing and imaging*; Artech House: Boston, 2009.
(6) Klimov, V. I. *Nanocrystal quantum dots*; 2nd ed.; CRC Press: Boca Raton, 2010.
(7) Na, H. B.; Song, I. C.; Hyeon, T. *Adv. Mater.* 2009, 21, 2133.
(8) Häfeli, U. *Scientific and clinical applications of magnetic carriers*; Plenum Press: New York, 1997.
(9) Dias, M. H. M.; Lauterbur, P. C. *Magn. Reson. Med.* 1986, 3, 328.
(10) Harisinghani, M. G.; Barentsz, J.; Hahn, P. F.; Deserno, W. M.; Tabatabaei, S.; van de Kaa, C. H.; de la Rosette, J.; Weissleder, R. *N. Engl. J. Med.* 2003, 348, 2491.
(11) Hyeon, T.; Lee, S. S.; Park, J.; Chung, Y.; Na, H. B. *J. Am. Chem. Soc.* 2001, 123, 12798.
(12) Park, J.; An, K.; Hwang, Y.; Park, J.-G.; Noh, H.-J.; Kim, J.-Y.; Park, J.-H.; Hwang, N. M.; Hyeon, T. *Nat. Mater.* 2004, 3, 891.
(13) Lee, J.-H.; Huh, Y.-M.; Jun, Y.-w.; Seo, J.-w.; Jang, J.-t.; Song, H.-T.; Kim, S.; Cho, E.-J.; Yoon, H.-G.; Suh, J.-S.; Cheon, J. *Nat. Med.* 2007, 13, 95.
(14) Jun, Y.-w.; Lee, J.-H.; Cheon, J. *Angew. Chem., Int. Ed.* 2008, 47, 5122.
15) Na, H. B.; Lee, I. S.; Seo, H.; Park, Y. I.; Lee, J. H.; Kim, S.-W.; Hyeon, T. *Chem. Commun.* 2007, 5167.
(16) Xu, C.; Xu, K.; Gu, H.; Zheng, R.; Liu, H.; Zhang, X.; Guo, Z.; Xu, B. *J. Am. Chem. Soc.* 2004, 126, 9938.
(17) Xie, J.; Xu, C.; Xu, Z.; Hou, Y.; Young, K. L.; Wang, S. X.; Pourmand, N.; Sun, S. *Chem. Mater.* 2006, 18, 5401.
(18) Xie, J.; Xu, C.; Kohler, N.; Hou, Y.; Sun, S. *Adv. Mater.* 2007, 19, 3163.
(19) Long, M. J. C.; Pan, Y.; Lin, H.-C.; Hedstrom, L.; Xu, B. *J. Am. Chem. Soc.* 2011, 133, 10006.
(20) Lee, H.; Dellatore, S. M.; Miller, W. M.; Messersmith, P. B. *Science* 2007, 318, 426.
(21) Amstad, E.; Gillich, T.; Bilecka, I.; Textor, M.; Reimhult, E. *Nano Lett.* 2009, 9, 4042.
(22) Wu, H.; Zhu, H.; Zhuang, J.; Yang, S.; Liu, C.; Cao, Y. C. *Angew. Chem., Int. Ed.* 2008, 47, 3730.
(23) Bae, K. H.; Kim, Y. B.; Lee, Y.; Hwang, J.; Park, H.; Park, T. G. *Bioconjugate Chem.* 2010, 21, 505.
(24) Kim, S.-W.; Kim, S.; Tracy, J. B.; Jasanoff, A.; Bawendi, M. G. *J. Am. Chem. Soc.* 2005, 127, 4556.
(25) Mei, B. C.; Susumu, K.; Medintz, I. L.; Delehanty, J. B.; Mountziaris, T. J.; Mattoussi, H. *J. Mater. Chem.* 2008, 18, 4949.
(26) Mei, B. C.; Oh, E.; Susumu, K.; Farrell, D.; Mountziaris, T. J.; Mattoussi, H. *Langmuir* 2009, 25, 10604.
(27) Stewart, M. H.; Susumu, K.; Mei, B. C.; Medintz, I. L.; Delehanty, J. B.; Blanco-Canosa, J. B.; Dawson, P. E.; Mattoussi, H. *J. Am. Chem. Soc.* 2010, 132, 9804.
(28) Xu, Y.; Qin, Y.; Palchoudhury, S.; Bao, Y. *Langmuir* 2011, 27, 8990.
(29) Tromsdorf, U. I.; Bigall, N. C.; Kaul, M. G.; Bruns, O. T.; Nikolic, M. S.; Mollwitz, B.; Sperling, R. A.; Reimer, R.; Hohenberg, H.; Parak, W. J.; Förster, S.; Beisiegel, U.; Adam, G.; Weller, H. *Nano Lett.* 2007, 7, 2422.
(30) Yi, D. K.; Lee, S. S.; Papaefthymiou, G. C.; Ying, J. Y. *Chem. Mater.* 2006, 18, 614.
(31) Nasongkla, N.; Bey, E.; Ren, J.; Ai, H.; Khemtong, C.; Guthi, J. S.; Chin, S.-F.; Sherry, A. D.; Boothman, D. A.; Gao, J. *Nano Lett.* 2006, 6, 2427.
(32) Kolb, H. C.; Finn, M. G.; Sharpless, K. B. *Angew. Chem., Int. Ed.* 2001, 40, 2004.
(33) Han, H.-S.; Devaraj, N. K.; Lee, J.; Hilderbrand, S. A.; Weissleder, R.; Bawendi, M. G. *J. Am. Chem. Soc.* 2010, 132, 7838.
(34) Texier, I. *Bioconjugate Chem.* 2010, 21, 583.
(35) Haun, J. B.; Devaraj, N. K.; Marinelli, B. S.; Lee, H.; Weissleder, R. *ACS Nano* 2011, 5, 3204.
(36) Hermanson, G. T. *Bioconjugate techniques*; 2nd ed.; Elsevier Academic Press: Amsterdam; Boston, 2008.
(37) Xing, Y.; Chaudry, Q.; Shen, C.; Kong, K. Y.; Zhau, H. E.; Chung, L. W.; Petros, J. A.; O'Regan, R. M.; Yezhelyev, M. V.; Simons, J. W.; Wang, M. D.; Nie, S. *Nat. Protocols* 2007, 2, 1152.
(38) Jung, C. W.; Jacobs, P. *Magn. Reson. Imaging* 1995, 13, 661.
(39) Rosenberg, J. T.; Kogot, J. M.; Lovingood, D. D.; Strouse, G. F.; Grant, S. C. *Magn. Reson. Med.* 2010, 64, 871.
(40) Wu, J.; Gao, C. *Macromol. Chem. Phys.* 2009, 210, 1697.

TABLE 1

| Abbreviations for chemicals | |
|---|---|
| Abbreviation | Name of chemical |
| PAA | polyacrylic acid |
| PEG | polyethylene glycol |
| DOPA | dopamine |
| DMAP | (4-(N,N-dimethylamino) pyridine) |
| DCC | N,N'-dicyclohexylcarbodiimide |
| DMF | dimethyl formamide |
| EDC | 3-dimethylaminopropyl-N'-ethylcarbodiimide |
| DMSO | Dimethyl sulfoxide |
| THF | tetrahydrofuran |

That which is claimed is:

1. A composition comprising:
nanoparticles coated with a coating composition, the coating composition comprising:
repeating polyacrylic acid monomer units covalently bound together in an aliphatic chain having a plurality of carboxylic acid functional groups and modified carboxylic acid functional groups extending therefrom, wherein a first portion of the modified carboxylic acid functional groups are modified by a PEG oligomer having a terminal methoxy functional group and a second portion of the modified carboxylic acid functional groups are modified by a PEG oligomer having at least one terminal catechol group.

2. The composition of claim 1, wherein the nanoparticles are coated by being directly bound to the at least one terminal catechol group.

3. The composition of claim 1, wherein the nanoparticles are magnetic.

4. The composition of claim 1, wherein the nanoparticles comprise iron oxide.

* * * * *